US012721873B2

(12) United States Patent
Gan et al.

(10) Patent No.: US 12,721,873 B2
(45) Date of Patent: Sep. 1, 2026

(54) ERGOTHIONEINE MICROCAPSULE STRUCTURE WITH PREBIOTICS, MANUFACTURING METHOD THEREOF AND ORAL DOSAGE FORM THEREOF

(71) Applicant: LeShroom Corporation Limited, Taipei City (TW)

(72) Inventors: Thiam-Chai Gan, Taipei City (TW); Jui-Tsung Chu, Taipei City (TW)

(73) Assignee: LESHROOM CORPORATION LIMITED, Taipei City (TW)

( * ) Notice: Subject to any disclaimer, the term of this patent is extended or adjusted under 35 U.S.C. 154(b) by 395 days.

(21) Appl. No.: 18/238,295

(22) Filed: Aug. 25, 2023

(65) Prior Publication Data

US 2024/0066084 A1 Feb. 29, 2024

(30) Foreign Application Priority Data

Aug. 26, 2022 (TW) .................................. 111132345

(51) Int. Cl.

*A61K 36/00* (2006.01)
*A61K 9/00* (2006.01)
*A61K 9/50* (2006.01)
*A61K 36/07* (2006.01)
*A61K 47/10* (2017.01)
*A61K 47/22* (2006.01)
*A61K 47/36* (2006.01)
*A61P 1/10* (2006.01)

(52) U.S. Cl.

CPC ............ *A61K 36/07* (2013.01); *A61K 9/0053* (2013.01); *A61K 9/5015* (2013.01); *A61K 47/10* (2013.01); *A61K 47/22* (2013.01); *A61K 47/36* (2013.01); *A61P 1/10* (2018.01); *A61K 2236/15* (2013.01); *A61K 2236/331* (2013.01); *A61K 2236/51* (2013.01); *A61K 2236/53* (2013.01)

(58) Field of Classification Search

CPC ...................................................... A61K 36/07
See application file for complete search history.

(56) References Cited

FOREIGN PATENT DOCUMENTS

CN 113491326 A * 10/2021 ............. A23L 27/20

OTHER PUBLICATIONS

Heisei 24 (received) No. 1204 Special Permit Bridge Infringement Request Incident Heisei 27 Jun. 5 The Second Small Court Judgment.

Heisei 24 (received) No. 2658 Concession Infringement Request Incident Heisei 27 Jun. 5 Second Small Court Judgment.

* cited by examiner

*Primary Examiner* — Qiuwen Mi
(74) *Attorney, Agent, or Firm* — MUNCY, GEISSLER, OLDS & LOWE, P.C.

(57) ABSTRACT

An ergothioneine microcapsule structure with prebiotics has a core layer and at least a coating layer, and the core layer has multiple holes. All of the holes are connected to each other, or all of the holes are not connected to each other, or a part of the holes are connected to each other, or a part of the holes are not connected to each other. The coating layer is formed by spraying concentrated liquid on all or a part of surfaces of the core layer and the holes. The concentrated liquid comprises prebiotics, such as polysaccharide, polyphenols and ergothioneine, and the core layer is formed by mushroom fruiting body particles. The present disclosure also illustrates a manufacturing method of the ergothioneine microcapsule structure with prebiotics, a usage of the ergothioneine microcapsule structure with prebiotics, and an oral dosage form of the ergothioneine microcapsule structure with prebiotics.

11 Claims, 8 Drawing Sheets

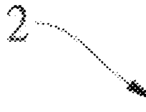

(a) providing mushroom fruiting body particles of at least a first mushroom fruiting body to form a core layer having multiple holes

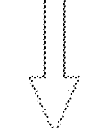

(b) using a granulation step to spray concentrated liquid on all or a part of surfaces of the core layer and the holes to form a coating layer, wherein the concentrated liquid comprises polysaccharide, polyphenols and ergothioneine, and a weight ratio of a weight of the coating layer over a weight of the core layer is 1:0.5 to 1:2.2.

FIG. 4

ERGOTHIONEINE MICROCAPSULE STRUCTURE WITH PREBIOTICS, MANUFACTURING METHOD THEREOF AND ORAL DOSAGE FORM THEREOF

TECHNICAL FIELD

The present disclosure relates to a microcapsule structure, and in particularly to, a microcapsule structure, a manufacturing method of the microcapsule structure, a usage of the microcapsule structure and an oral dosage form of the microcapsule structure, wherein the microcapsule structure has a core layer and a coating layer, the core layer is formed by mushroom fruiting body particles, and the coating layer is formed on the surface of the core layer and comprises polysaccharide, polyphenols and ergothioneine.

RELATED ART

In health supplements, mushrooms have been one of the food materials favored by people since ancient times, and mushrooms are rich in various functional components, which have the health benefits of enhancing physical strength, improving immunity, anti-cancer, regulating blood sugar and blood lipids. Among the functional ingredients of mushrooms, ergothioneine has gradually attracted people's attention for its powerful antioxidant activity and anti-inflammatory ability. In addition, the polysaccharide of mushrooms also has beneficial effects on human health, such as lowering blood sugar, lowering cholesterol, immune regulation, and adjusting intestinal bacteria to promote intestinal peristalsis.

Ergothioneine cannot be synthesized in animals or plants, and can only be obtained through diet, and taking mushrooms is the most effective way to obtain ergothioneine. However, to obtain enough concentration of the ergothioneine for human health benefits, many mushrooms must be required. However, mushrooms are high-potassium foods, which are not suitable for kidney patients with high blood potassium and gout patients with high uric acid. On the other hand, mushrooms have thick cell walls, and it is difficult for the human body to digest, and if it is taken too much, it will easily increase the burden on the stomach and cause gastrointestinal discomfort. Moreover, ergot sulfur itself is a highly water-soluble component, and if it is not cooked properly, it will easily lead to loss nutrient content.

Therefore, the present disclosure is to describe how to effectively improve the inconvenience of taking ergothioneine directly through cooking mushrooms through the innovative design, so that users can more easily take enough prebiotics such as ergothioneine, polyphenols and polysaccharides to improve intestinal function and reduce the occurrence of constipation.

SUMMARY

To solve the inconvenience or excessive consumption of a large number of mushrooms in the past, the present disclosure provides an ergothioneine microcapsule structure with prebiotics, a manufacturing method of the ergothioneine microcapsule structure with the prebiotics, a usage of the ergothioneine microcapsule structure with the prebiotics and an oral dosage form of the ergothioneine microcapsule structure with the prebiotics. By increasing the content of polysaccharide, polyphenols and ergothioneine that each microcapsule structure contains, it ensures that the microcapsules contain a sufficient concentration of medicinal active ingredients, and it reduces the accompanying shortcomings of direct intake of mushrooms.

An objective of the present disclosure is to provide an ergothioneine microcapsule structure with prebiotics, and the ergothioneine microcapsule structure with the prebiotics comprises at least a core layer and at least a coating layer. The core layer has multiple holes, wherein all of the holes are connected to each other, or all of the holes are not connected to each other, or a part of the holes are connected to each other, or a part of the holes are not connected to each other. The coating layer is formed by spraying concentrated liquid on all or a part of surfaces of the core layer and the holes.

In an embodiment of the present disclosure, the concentrated liquid comprises polysaccharide, polyphenols and ergothioneine, and the core layer is formed by mushroom fruiting body particles.

In an embodiment of the present disclosure, a shape of the core layer is an irregular structure, a sphere, an ellipsoid, a cylinder or a polyhedron.

In an embodiment of the present disclosure, the ergothioneine microcapsule structure with the prebiotics is formed by multiple core layers coated with multiple coating layers, wherein all or a part of the core layers have identical or different particle sizes.

In an embodiment of the present disclosure, the core layer is obtained by freeze-drying.

In an embodiment of the present disclosure, a weight ratio of a weight of the coating layer over a weight of the core layer is 1:0.5 to 1:2.2.

Another objective of the present disclosure is to provide a usage of the above ergothioneine microcapsule structure with the prebiotics for improving constipation and cleansing the colon.

Another objective of the present disclosure is to provide a manufacturing method of an ergothioneine microcapsule structure with prebiotics, comprising steps as follow: (a) providing mushroom fruiting body particles of at least a first mushroom fruiting body to form a core layer. wherein the core layer has multiple holes; and (b) using a granulation step to spray concentrated liquid on all or a part of surfaces of the core layer and the holes to form a coating layer, wherein the concentrated liquid comprises polysaccharide, polyphenols and ergothioneine, and a weight ratio of a weight of the coating layer over a weight of the core layer is 1:0.5 to 1:2.2.

In an embodiment of the present disclosure, a pulverization step, an extraction step and a concentration step are sequentially performed on a second mushroom fruiting body to form the concentrated liquid.

In an embodiment of the present disclosure, the pulverization step is to add the second mushroom fruiting body into a solvent to form a mushroom mixture and then to pulverize the second mushroom fruiting body of the mushroom mixture, wherein the mushroom mixture is 100 parts by weight, including 10-80 parts by weight of the second fruiting mushroom body, and the balance is the solvent, which is pure water or 20%-95% ethanol solution.

In an embodiment of the present disclosure, the extraction step comprises a hot water extraction step or an ultrasonic extraction step and a centrifugation step, wherein the hot water extraction step or the ultrasonic extraction step is to extract the pulverized mushroom mixture to obtain first extract, and the centrifugation step is to centrifuge the first extract to collect supernatant as second extract, wherein an extraction time of the extraction step is 0.5-24 hours.

In an embodiment of the present disclosure, the concentration step comprises a decompression concentration step or heating concentration step, which is used to concentrate the second extract to obtain the concentrated liquid, wherein a ratio of a weight of the concentrated liquid over a weight of the second mushroom fruiting body is 0.1 to 0.3.

In an embodiment of the present disclosure a freeze-drying step and a dry-milling step are sequentially performed on the first mushroom fruiting body to obtain the mushroom fruiting body particles of the first mushroom fruiting body.

In an embodiment of the present disclosure, the freeze-drying step is to freeze the first mushroom fruiting body at a freezing temperature, and the freezing temperature is −20 degrees Celsius to −80 degrees Celsius.

In an embodiment of the present disclosure, the dry-milling step is to utilize a dry grinding manner to grind the frozen first mushroom fruiting body into the mushroom fruiting body particles of the first mushroom fruiting body.

In an embodiment of the present disclosure, the grinded first mushroom fruiting body is screened by using a first mesh screen to obtain the mushroom fruiting body particles of the first mushroom fruiting body, and the first mesh screen has 80 meshes per inch.

In an embodiment of the present disclosure, multiple core layers coated with multiple coating layers are screened by a second mesh screen to obtain the ergothioneine microcapsule structure with the prebiotics, and the second mesh screen has 60 meshes per inch.

In an embodiment of the present disclosure, each of the first mushroom fruiting body and the second mushroom fruiting body comprises at least one of a shiitake mushroom, an enoki mushroom (i.e., *Flammulina velutipes*), a king oyster mushroom (i.e., *Pleurotus eryngii*) and a corn mushroom.

Another objective of the present disclosure is to provide an oral dosage form, and the oral dosage form comprises multiple ergothioneine microcapsule structures with prebiotics, wherein each of the ergothioneine microcapsule structures with the prebiotics is formed by the above manufacturing method of the ergothioneine microcapsule structure with the prebiotics, and the oral dosage form is selected from a gelatin capsule or a non-gelatin capsule.

Accordingly, in the present disclosure, the microcapsule structure comprises the core layer and the coating layer, wherein the core layer is formed by the mushroom fruiting body particles, and the surface of the coating layer is formed with polysaccharide, polyphenols and ergothioneine. Therefore, by increasing the surface area or filling capacity of the coating layer to increase the content of polysaccharide, polyphenols and ergothioneine contained in each microcapsule structure, it ensures that the microcapsule structure has the concentration of medicinal active ingredients that have health effects on the human body, and the inconvenience of having to eat a large amount of mushrooms in the past or the disadvantage of eating too much can be solved.

BRIEF DESCRIPTIONS OF DRAWINGS

The present disclosure can be more fully understood by reading the subsequent detailed description and examples with references made to the accompanying drawings, wherein dimensions and arrangement configurations in the drawings are for illustration only, and the present disclosure is not limited thereto. Each figure of the drawings is briefly illustrated as follows.

FIG. 4 is a flow chart of a manufacturing method of an ergothioneine microcapsule structure with prebiotics according to an embodiment of the present disclosure.

DETAILS OF EXEMPLARY EMBODIMENTS

The following description is of the best-contemplated mode of conducting the present disclosure. This description is made for the purpose of illustrating the general principles of the present disclosure and should not be taken in a limiting sense. The scope of the present disclosure is best determined by reference to the appended claims.

To make the narration of the present disclosure more detailed and complete, the following provides illustrative descriptions for specific embodiments and implementations of the present disclosure. However, the following embodiments and implementations are not the only form of implementing or using the technology of the present disclosure.

In the present disclosure, when the expression of the singular form is not specifically mentioned, the singular form also includes the concept of the plural form. In addition, the terms used in the present disclosure should be understood to be used in the meanings commonly used in the relevant field unless otherwise mentioned. Therefore, unless otherwise defined, all technical and scientific terms used in the present disclosure have the same meaning as generally understood by those skilled in the art to which the present disclosure belongs.

Figure 1:
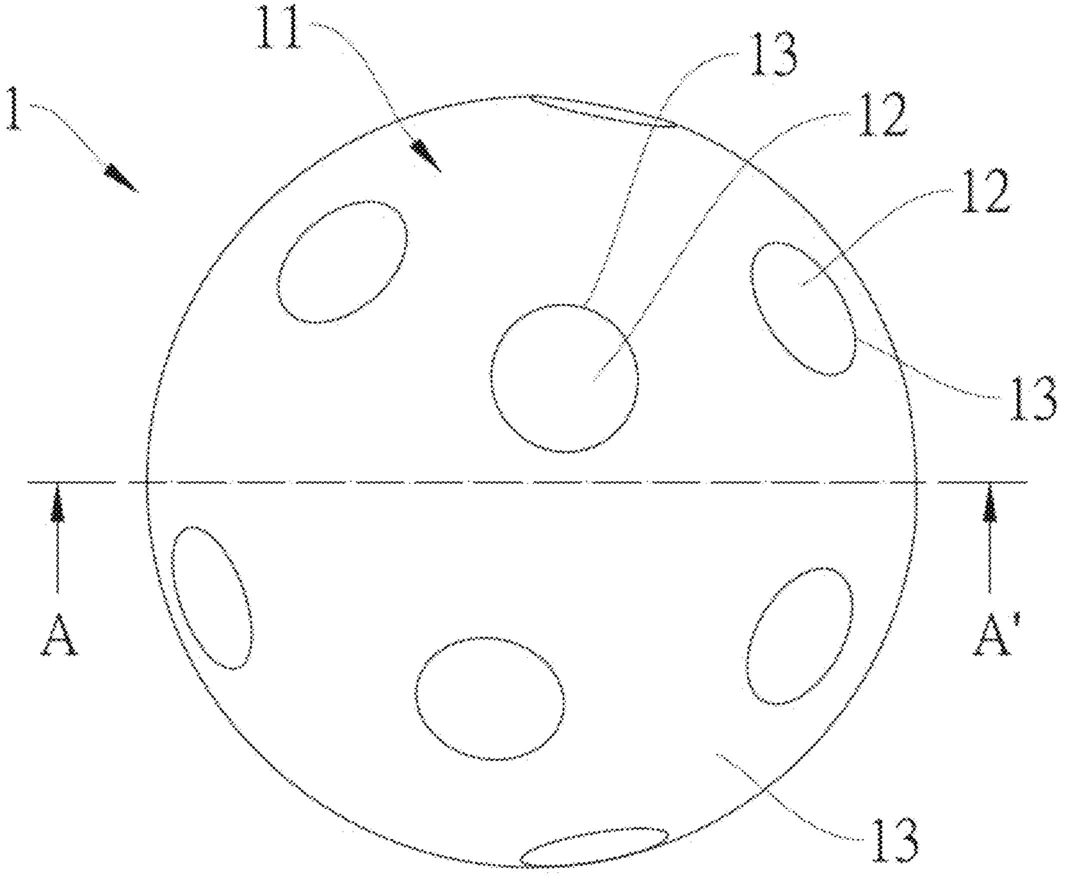
FIG. 1 is a schematic diagram showing an ergothioneine microcapsule structure with prebiotics according to an embodiment of the present disclosure.

Refer to FIG. 1, and a main objective of the present disclosure is to provide an ergothioneine microcapsule structure with prebiotics. In the present disclosure, mushroom fruiting body particles are utilized to form a core layer (11), and concentrated liquid is spray on surfaces of the core layer (11) and holes (12) of the core layer (11) to form a coating layer (13), wherein the concentrated liquid comprises prebiotics, such as polysaccharide, polyphenols and ergothioneine. The holes (12) can increase attaching surface area or filling capacity of polysaccharide, polyphenols and ergothioneine, such that the contents of polysaccharide, polyphenols and ergothioneine contained in each microcapsule structure can be increased. In the present disclosure, the microcapsule structure is purposefully selected, so that mushroom fruiting body particles, polysaccharide, polyphenols and ergothioneine can be effectively released, and the dissolution rate is increased, which is conducive to human absorption.

In an embodiment of the present disclosure, a shape of the core layer (11) is an irregular structure, a sphere, an ellipsoid, a cylinder or a polyhedron, wherein the irregular structure is a structure with at least an irregular surface. The core layer (11) has multiple holes (12), wherein all of the holes (12) are connected to each other, or all of the holes (12) are not connected to each other, or a part of the holes (12) are connected to each other, or a part of the holes (12) are not connected to each other. The coating layer (13), formed by spraying concentrated liquid on all or a part of surfaces of the core layer (11) and the holes (12). All or a part of the surface of the core layer (11) also comprises all or a part of the surfaces of the holes (12), wherein the holes (12) of the core layer (11) and the irregular surface structure can increase the adsorption capacity of coating layer (13).

Figure 2A:
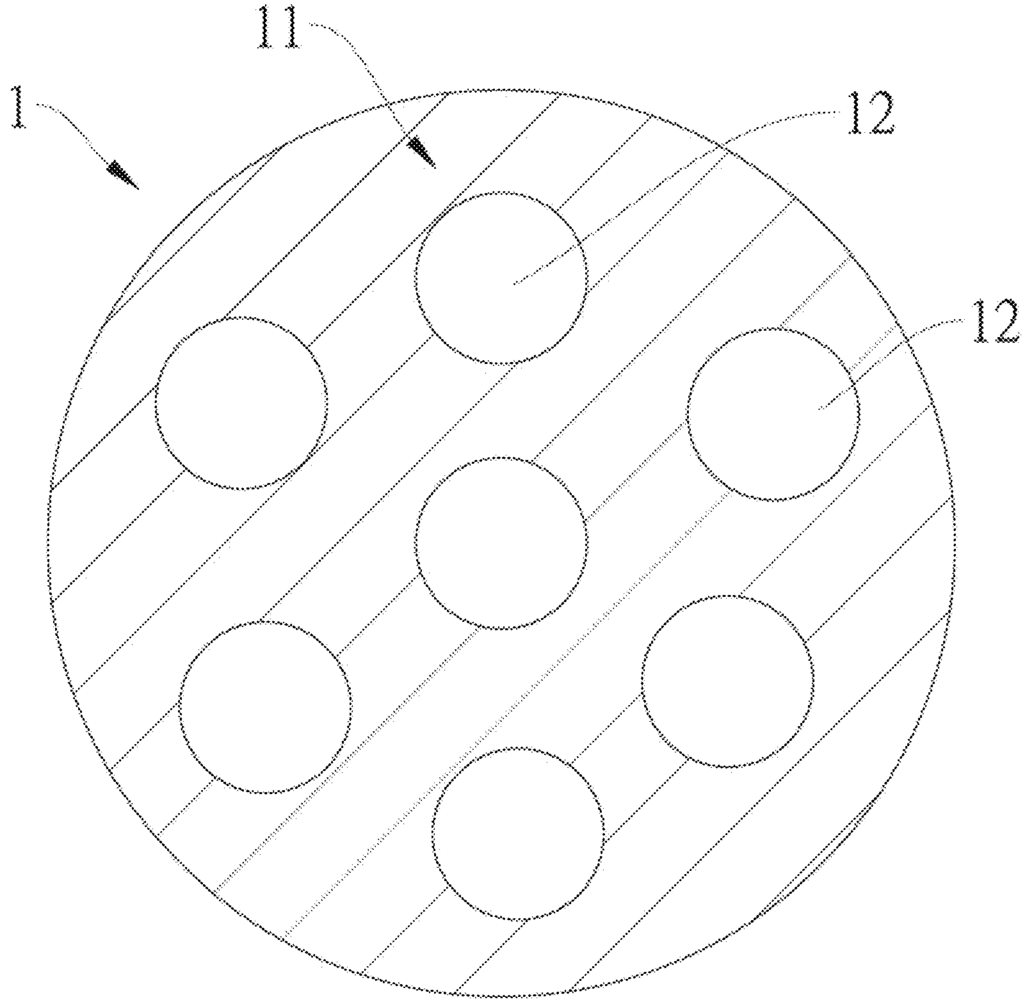
FIG. 2A is a sectional view of a core layer of an ergothioneine microcapsule structure with prebiotics according to an embodiment of the present disclosure.
Figure 2B:
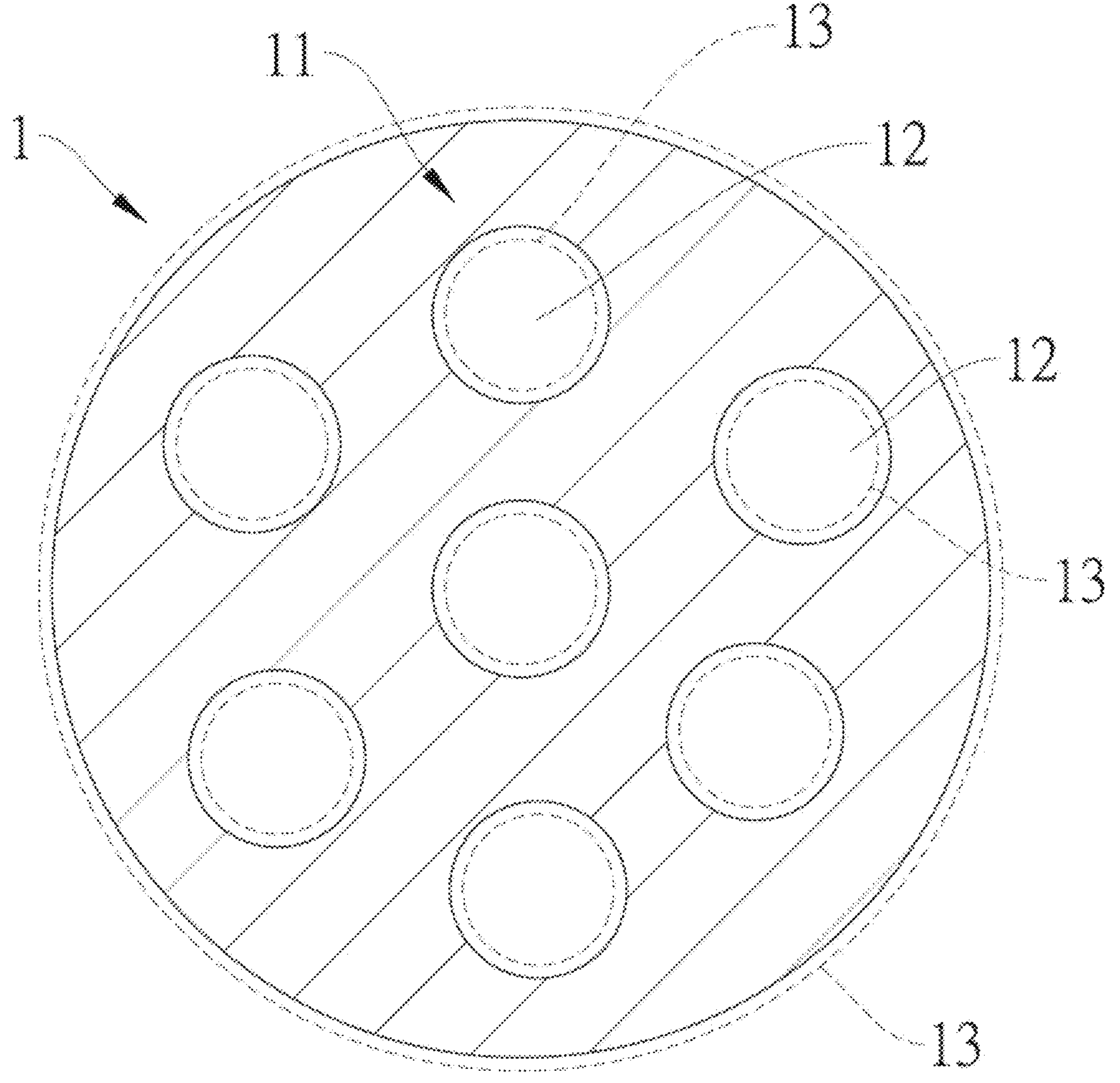
FIG. 2B is a sectional view of an ergothioneine microcapsule structure with prebiotics according to an embodiment of the present disclosure.
Figure 3A:
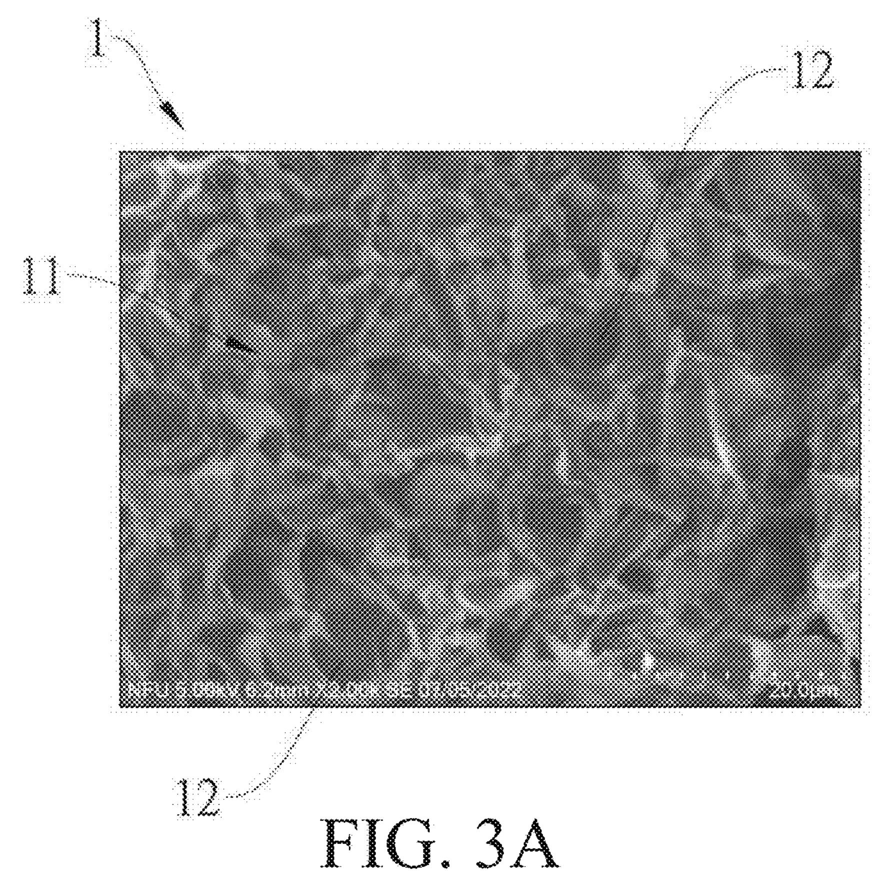
FIG. 3A is an enlarged view of a core layer of an ergothioneine microcapsule structure with prebiotics by using a scanning electron microscope (SEM) according to an embodiment of the present disclosure.
Figure 3B:
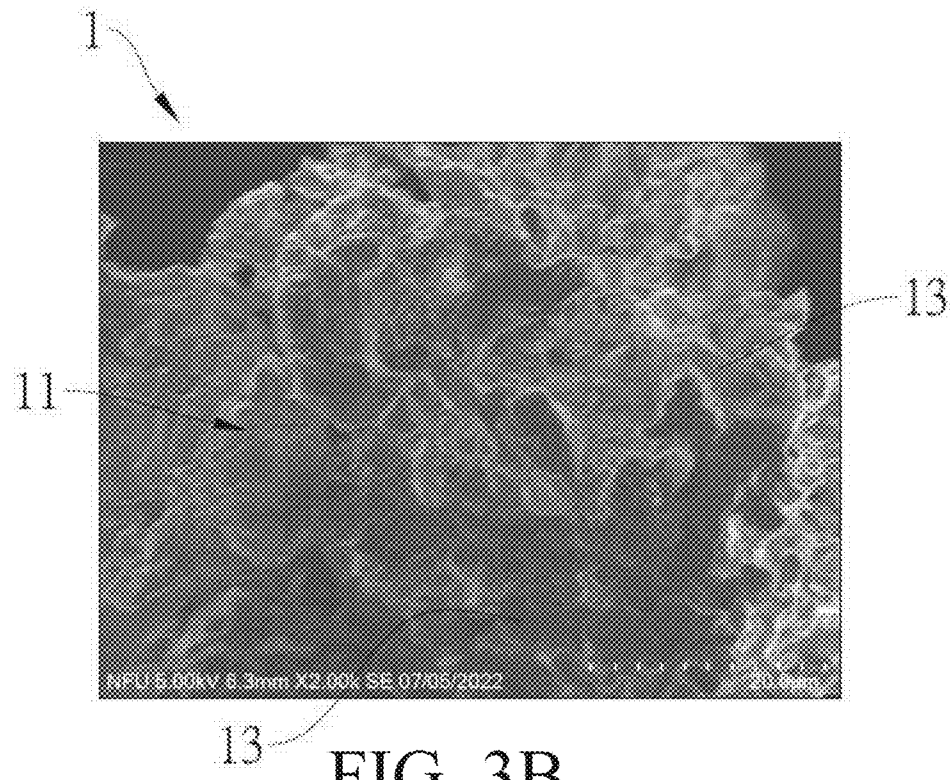
FIG. 3B is an enlarged view of an ergothioneine microcapsule structure with prebiotics by using a scanning electron microscope (SEM) according to an embodiment of the present disclosure.

Refer to FIG. 2A, in an embodiment of the present disclosure, the shape of the core layer (11) is a sphere with holes (12), and all of the holes (12) are not connected to each other. Refer to FIG. 2B, and FIG. 2B is sectional view of a section line A-A' in FIG. 1. The surfaces of the core layer (11) and the holes (12) are formed with the coating layer (13). The concentrated liquid comprises prebiotics, such as polysaccharide, polyphenols and ergothioneine. For example, the concentrated liquid is a concentrated liquid extracted from dry powders of at least one of a shiitake mushroom, an enoki mushroom, a king oyster mushroom and a corn mushroom, and the present disclosure is not limited thereto. The core layer (11) is formed by mushroom fruiting body particles. The core layer (11) is for example formed by a king oyster mushroom or a corn mushroom, and the present disclosure is not limited thereto. As shown in FIG. 3A and FIG. 3B, the core layer (11) and the ergothioneine microcapsule structure with prebiotics are observed by a scanning electron microscope (SEM) to obtain their enlarged views, wherein the scale bar is 20.0 μm. In FIG. 3A, the magnification of the SEM is 2000 times, and the core layer (11) made of the mushroom fruiting body particles of the king oyster mushrooms is observed. In the enlarged view, after the freeze-drying process is performed, the shape of the core layer (11) is an irregular structure with the holes (12), wherein the irregular structure is a three-dimensional structure, and all of the holes (12) are connected to each other, or all of the holes (12) are not connected to each other, or a part of the holes (12) are connected to each other, or a part of the holes (12) are not connected to each other. In FIG. 3B, the magnification of the SEM is also 2000 times, for one microcapsule structure, the core layer (11) made of the mushroom fruiting body particles of the king oyster mushrooms and the coating layer (13) are observed. In the enlarged view, the surfaces of the core layer (11) and the holes (12) are formed with the coating layer (13). It is noted that, the freeze-drying process can prevent the destruction of the active ingredient structure in the core layer (11), and thus it ensures that the chemical structure will not be destroyed, and medicinal activity can be kept.

The ergothioneine microcapsule structure (1) with the prebiotics can be formed by multiple core layers (11) coated with multiple coating layers (13), wherein all or a part of the core layers (11) have identical or different particle sizes, and the coating layers (13) can be made of different mushroom fruiting body particles. The core layers (11) having identical or different particle sizes can be screened out by mesh screens having 60 and 80 meshes per inch, such that the ergothioneine microcapsule structure with the prebiotics, which has an average particle size of 180 μm to 250 μm, can be obtained, and a weight ratio of a weight of the coating layer (13) over a weight of the core layer (11) being 1:0.5 to 1:2.2 can be indirectly controlled.

Refer to FIG. 3A and FIG. 4, another main objective of the present disclosure is to provide a manufacturing method (2) of the ergothioneine microcapsule structure with the prebiotics. The manufacturing method (2) of the ergothioneine microcapsule structure with the prebiotics comprises steps (a) and (b). At step (a), mushroom fruiting body particles of at least a first mushroom fruiting body are provided to form a core layer (11), wherein the core layer (11) has multiple holes (12), and a freeze-drying step and a dry-milling step are sequentially performed on the first mushroom fruiting body to obtain the mushroom fruiting body particles of the first mushroom fruiting body. Thus, the shape of the core layer (11) is the irregular structure, and the core layer (11) has the holes (12), wherein all of the holes (12) are connected to each other, or all of the holes (12) are not connected to each other, or a part of the holes (12) are connected to each other, or a part of the holes (12) are not connected to each other, as shown in FIG. 2A. The freeze-drying step is to freeze the first mushroom fruiting body at a freezing temperature, and the freezing temperature is −20 degrees Celsius to −80 degrees Celsius, so as to reduce residual fluid. The freeze-drying step can not only reduce the damage to the structure of the core layer (11), thereby maintaining the chemical structure and medicinal activity of the mushroom fruiting body particles, but also prolong the shelf life for subsequent processing. The dry-milling step is to utilize a dry grinding manner to grind the frozen first mushroom fruiting body into the mushroom fruiting body particles of the first mushroom fruiting body. The dry grinding manner can produce particles through the high-speed impact of the first mushroom fruiting body and the knife, and then use the centrifugal principle of the cyclone separator or jet mill to discharge the grinded particles. The core layer (11) can be, for example but not limited to, made of the king oyster mushroom or corn mushroom.

Refer to FIG. 3B and FIG. 4, at step (b), a granulation step is used to spray concentrated liquid on all or a part of surfaces of the core layer (11) and the holes (12) to form a coating layer (13), wherein the holes (12) and the irregular surface structure of the core layer (11) can increase the adsorption capacity of the coating layer (13). The granulation step can be a spray granulation step, which can be carried out through the spray dryer, wherein the internal temperature of the spray dryer and the nozzle temperature can be adjusted according to actual needs. By using the spray granulation step, in addition to obtaining free-flowing powder particles, it also avoids the destruction of the medicinal activity of the medicinal ingredients of the ergothioneine microcapsule structure with prebiotics during the spray-drying process. The concentrated liquid comprises polysaccharide, polyphenols and ergothioneine, and a weight ratio of a weight of the coating layer (13) over a weight of the core layer (11) is 1:0.5 to 1:2.2. In practice, in addition to retaining a relatively high content of polysaccharide, polyphenols and ergothioneine, it also maintains the release time and blood concentration of these medicinal active ingredients in the human body to achieve the maximum effect. The concentrated liquid can be exemplified but not limited to the concentrated liquid extracted from dried powder of the shiitake mushroom, the enoki mushroom, the king oyster mushroom or the corn mushroom.

In an embodiment of the present disclosure, a pulverization step, an extraction step and a concentration step are sequentially performed on a second mushroom fruiting body of at least one kind to form the concentrated liquid.

The pulverization step is to add the second mushroom fruiting body into a solvent to form a mushroom mixture and then to pulverize the second mushroom fruiting body of the mushroom mixture, wherein the mushroom mixture is 100 parts by weight, including 10-80 parts by weight of the second fruiting mushroom body, and the balance is the solvent, which is pure water or 20%-95% ethanol solution. Preferably, the solvent is 50%-70% ethanol solution. The pure water or ethanol solution is the more hydrophilic solvent, and in practice, according to the different weight parts of the mushroom fruiting body, the pure water or the ethanol solution of suitable concentration for extraction is selected as the solvent for sequential extraction. The second mushroom fruiting body is for example a shiitake mushroom, an enoki mushroom, a king oyster mushroom and a corn mushroom, and the present disclosure is not limited thereto.

The extraction step comprises a hot water extraction step or an ultrasonic extraction step and a centrifugation step. The hot water extraction step or the ultrasonic extraction step is to extract the pulverized mushroom mixture to obtain first extract, wherein an extraction time of the extraction step is 0.5-24 hours. When the pure water is selected as the solvent, the hot water extraction step is executed, and when the ethanol solution is selected as the solvent, the ultrasonic extraction step is executed. The hot water extraction step and the ultrasonic extraction step are performed at a heating temperature of 60 degrees Celsius to 80 degrees Celsius to extract the pulverize mushroom mixture, and an extraction time is 0.5 to 24 hours, so as to obtain a higher content of active ingredients. The centrifugation step is to centrifuge the first extract obtain second extract. A centrifugation temperature at the centrifugation step is 4 degrees Celsius, a centrifugation speed is 9000 rpm (revolution(s) per minute), the first extract is centrifuged for 15 minutes to collect supernatant, and the supernatant is the second extract which comprises polysaccharide, polyphenols and ergothioneine.

The concentration step comprises a decompression concentration step or heating concentration step, which is used to concentrate the second extract to obtain the concentrated liquid, wherein the decompression concentration step or heating concentration step is to concentrate the second extract under certain conditions of a pressure, a temperature and a time to remove excess solvent, such that the weight of the concentrated liquid is 0.1 to 0.3 times of the weight of the second mushroom fruiting body. The concentration step concentrates the second extract extracted from the second mushroom fruiting body, such that in the subsequent preparation of the coating layer (13), a certain content and concentration of active ingredients can be maintained.

Another main objective of the present disclosure is to provide an oral dosage form, and the oral dosage form comprises multiple ergothioneine microcapsule structures (1) with prebiotics, wherein each of the ergothioneine microcapsule structures (1) with the prebiotics is formed by the manufacturing method (2) of the ergothioneine microcapsule structure (1) with the prebiotics. The oral dosage form is selected from a gelatin capsule or a non-gelatin capsule. A material for the gelatin capsule can be selected from polyethylene glycol (PEG), sorbitol, glycerin, polypropylene glycol and other polyols. A material of the non-gelatin capsule can be selected from starch, starch derivatives, cellulose, cellulose esters, cellulose ethers, cellulose nitrates, cellulose triacetates, cellulose acetate phthalate (CAP), methylcellulose, ethyl cellulose, hydroxypropyl methyl cellulose (HPMC), hydroxypropyl Cellulose (HPC) and hydroxypropyl methyl cellulose phthalate (HPMCP). In practice, the ergothioneine microcapsule structure (1) with the prebiotics of the present disclosure can also be used in oral dosage forms of capsules of different types according to the needs of users. For example, oral dosage form of non-gelatin capsules can be used in consideration of the potential allergies of animal sources, religious belief and vegetarian.

Another main objective of the present disclosure is to provide a usage of the ergothioneine microcapsule structure (1) with the prebiotics for improving constipation and cleansing the colon.

In the following experimental test, 24 voluntary subjects with constipation problem are divided into an experimental group and a control group, wherein 12 voluntary subjects of the experimental group take the ergothioneine microcapsule structures with the prebiotics provided by the present disclosure, and 12 voluntary subjects of the control group take the general mushroom powder capsules. The ergothioneine microcapsule structure with the prebiotics of the present disclosure comprises a core layer and a coating layer, the core layer is made of mushroom fruiting body particles, and the concentrated liquid is sprayed on the surface of the core layer to form the coating layer. The general mushroom powder capsule is composed of maltodextrin and mushroom concentrated liquid. In each of the experimental group and the control group, there are two men of 40-50 years old, two men of 60-70 years old, 4 women of 40-50 years old and 4 women of 60-70 years old, i.e., total 12 persons. Before taking capsules, the voluntary subjects first fill in the intestinal age questionnaire (please refer to TABLE 1), and the relevant data of defecation is then counted. The intestinal age questionnaire is based on the evaluation made by Dr. Benno Yoshiki who is the office chief of Laboratory of Microbial Function Analysis, RIKEN. The test is lasted for 4 weeks. The voluntary subjects take the capsules in the morning and evening after meals. Each of the voluntary subjects of the experimental group takes 4 ergothioneine capsules of the present disclosure (500 mg/capsule, and each capsule comprises multiple ergothioneine microcapsule structure with prebiotics) one day. Each of the voluntary subjects of the control group takes 4 general mushroom powder capsules (500 mg/capsule) one day. After 4 weeks of taking capsules elapses every day, the voluntary subjects of the two groups fill in the intestinal age questionnaire according to their somatosensory degree, and then the relevant data of defecation is then counted.

TABLE 1

| Answer | Question |
|---|---|
| ☐Yes ☐No | (1) Difficulty defecating without exerting force |
| ☐Yes ☐No | (2) Feeling unclean even after going to the toilet |
| ☐Yes ☐No | (3) The stool is hard to pass |
| ☐Yes ☐No | (4) The defecation presents lumps |
| ☐Yes ☐No | (5) Sometimes the stool is soft or diarrhea |
| ☐Yes ☐No | (6) The color of the stool is very dark and black |
| ☐Yes ☐No | (7) Defecation and exhaust are very smelly |
| ☐Yes ☐No | (8) Defecation time is indefinite |
| ☐Yes ☐No | (9) Defecation sinks to the bottom of the toilet |
| ☐Yes ☐No | (10) Defecation frequency at least once a day |

The relevant data of defecation of the test is counted and analyzed. In the test, whether constipation is improved is evaluated based on the questions (1)-(4) of the intestinal age questionnaire, the questions (1)-(4) are respectively "difficulty defecating without exerting force", "feeling unclean even after going to the toilet", "the stool is hard to pass" and "the defecation presents lumps". If the answer of each of the questions (1)-(4) answered by the voluntary subject is yes, the score of the question is 1, and the scores of the questions (1)-(4) of the voluntary subjects added up to obtain a total score of the questions (1)-(4) of the voluntary subjects. Then, an equation is used to calculate an index value according to the total score of the questions (1)-(4) of the voluntary subjects. The equation is the total score of the questions (1)-(4) of the voluntary subjects of the group over the product of the voluntary subject number of the group and the question number of the questions (1)-(4) (i.e., 12*4 in the test). The improvement is the index value before taking capsules minus the index value after taking capsules.

Figure 5A:
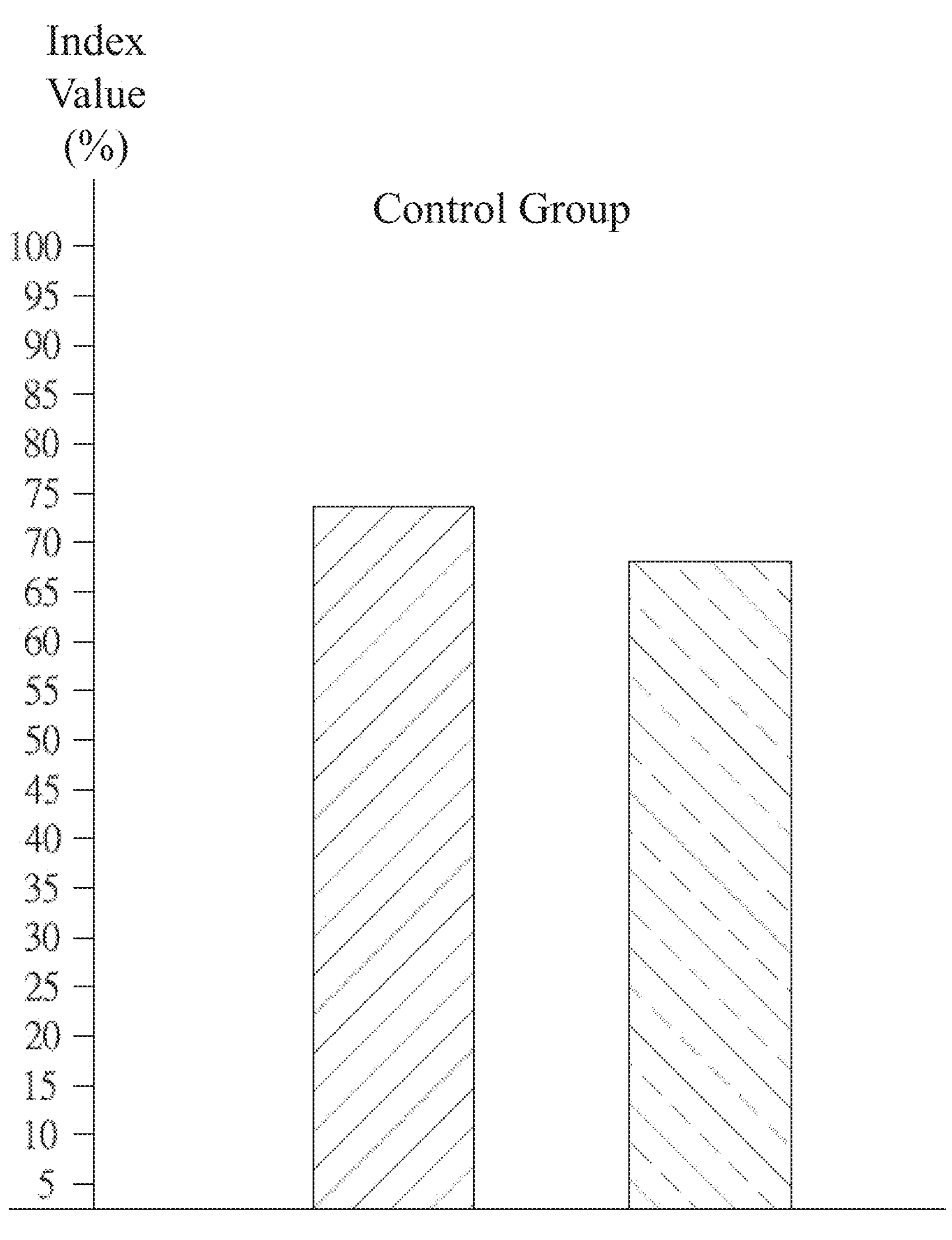
FIG. 5A is a data chart of questionnaire survey results for defecation status after and before subjects take general mushroom powder capsules.
Figure 5B:
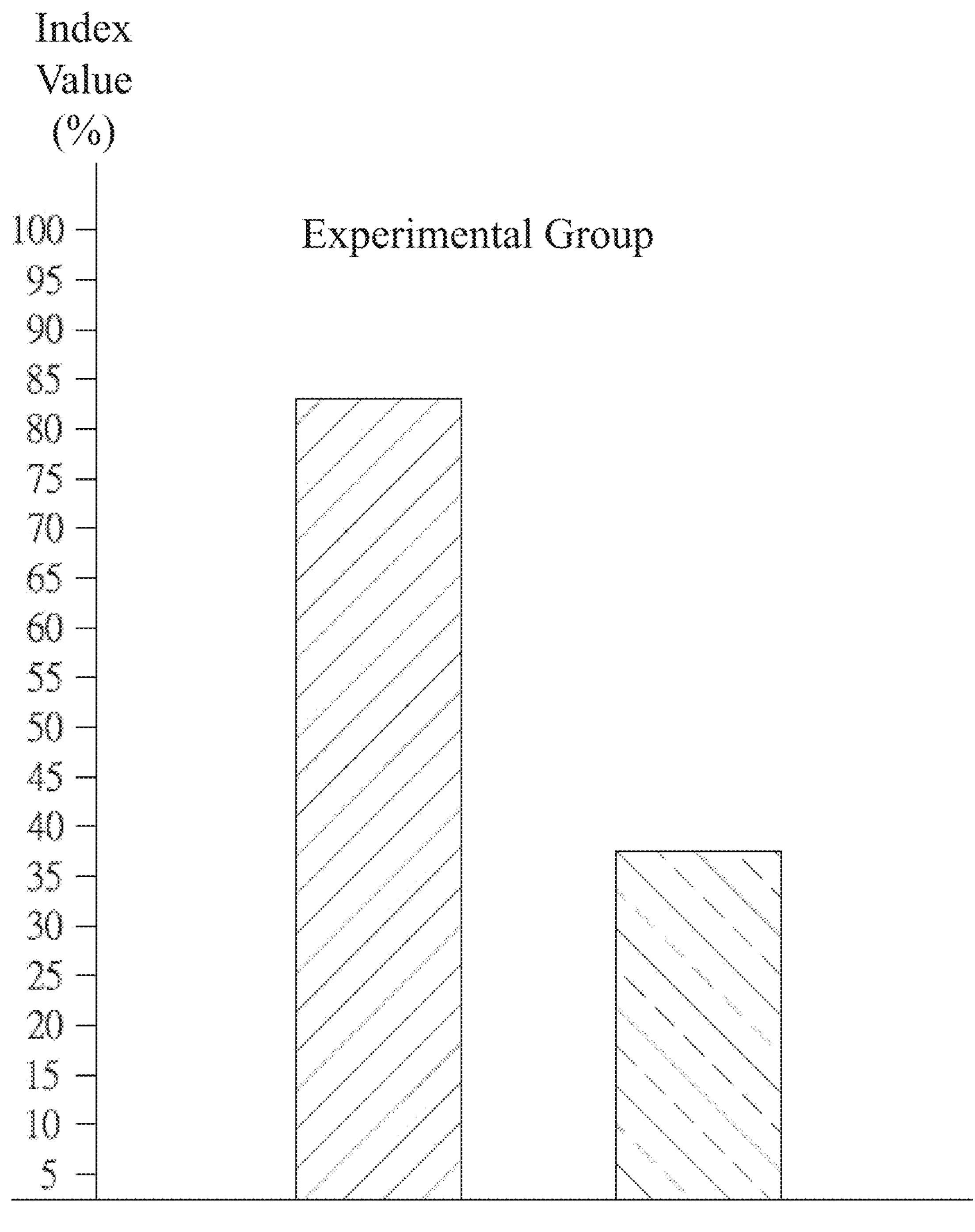
FIG. 5B is a data chart of questionnaire survey results for defecation status after and before subjects take ergothioneine microcapsule structures with prebiotics according to an embodiment of the present disclosure.

The test result is described as follows. Refer to FIG. 5A, FIG. 5B and TABLE 2, and TABLE 2 shows the index values of the experimental group and the control group before/after taking capsules, and the improvements of the experimental group and the control group after taking capsules. FIG. 5A is a data chart of questionnaire survey results for defecation status after and before subjects take general mushroom powder capsules, and FIG. 5B is a data chart of questionnaire survey results for defecation status after and before subjects take ergothioneine microcapsule structures with prebiotics according to an embodiment of the present disclosure. The X axis presents the index of before taking capsules and the after before taking capsules, and the Y axis presents the index value. From the test result, the index values of the experimental group and the control group before taking capsules are respectively 77% and 69%. After taking capsules for 4 weeks, as shown in FIG. 5A, the index value of the control group (taking general mushroom powder capsules) is maintained about 65%, and the improvement is merely 4%. However, taking capsules for 4 weeks, as shown in FIG. 5B, the index value of the experimental group (taking the ergothioneine microcapsule structure with the prebiotics) is decreased to 27%, and the improvement is 50%. Accordingly, after taking the ergothioneine microcapsule structure with the prebiotics of the present disclosure, it has the effects of improving constipation and cleansing the colon. In particular, the operation of the digestive organs of the human body will not only be affected by the relationship between diet and daily life, but also with age, the digestive organs will gradually begin to age, resulting in problems with bowel movements. However, the ergothioneine microcapsule structure with the prebiotics of the present disclosure can improve constipation and cleanse the colon for the mem or women of 40-70 years old.

TABLE 2

| | Before taking Index value (%) | After taking Index value (%) | Improvement (%) |
|---|---|---|---|
| Control group | 69% | 65% | 4% |
| Experimental group | 77% | 27% | 50% |

Then, in order to enable the person with the ordinary skill in the art to further understand the purpose of the present disclosure, characteristics, and the effect to be achieved, details of the manufacturing method of the ergothioneine microcapsule structure with the prebiotics mentioned in the present disclosure is described below, to confirm that through the present disclosure, the ergothioneine microcapsule structure with the prebiotics of the present disclosure is rich in polysaccharide, polyphenols and ergothioneine. The application of practical applicability of the present disclosure is also demonstrated as follows, and the application of the present disclosure is not intended to limit the scope of the disclosure in any way.

In Embodiment 1, mushrooms of various kinds are used to prepare concentrated liquid, and the ergothioneine content is also tested. Details of Embodiment 1 are illustrated as follows.

The preparation of Embodiment 1 is illustrated as follows. At least one of the shiitake mushroom, the enoki mushroom, the king oyster mushroom and the corn mushroom is taken as raw material, the raw material is weighted, and the king oyster mushroom, the corn mushroom, the shiitake mushroom or the enoki mushroom dry powder of 1 kg is obtained. Then, the king oyster mushroom, the corn mushroom, the shiitake mushroom or the enoki mushroom dry powder of 1 kg is added in an extract solvent of 10 liters, wherein the extract solvent is pure water or 95% ethanol solution. Next, the above solution is uniformly mixed for 5 minutes through a homogenizer to obtain a homogeneous liquid. First extract is obtained by extracting the homogeneous liquid for 30 to 60 minutes through a food-grade ultrasonic extraction machine with an ultrasonic frequency range of 35 KHZ, a power of 180 W, and an extraction temperature of 60 degrees Celsius. The first extract is centrifuge at 4 degrees Celsius at a speed of 9000 rpm for 15 minutes, then the supernatant is collected, and the supernatant is the second extract of the shiitake mushroom, the enoki mushroom, the king oyster mushroom or the corn mushroom. Next, the second extract is concentrated to 1 liter under a decompression temperature of 40 to 60 degrees Celsius through a decompression concentrator, so as to obtain the concentrated liquid.

Ergothioneine content test in Embodiment 1 is illustrated as follows.

An ultra-high pressure liquid chromatography (UPLC) is used to perform the content analysis of the ergothioneine on the concentrated liquid, and the ergothioneine obtained from each concentrated liquid is quantitatively analyzed through the calibration line prepared by ergothioneine standard substances with different concentrations. The analysis conditions of the ultra-high pressure liquid chromatography are as described as follows. The system is waters acquisition UPLC H-Class, the detector is a photodiode array detector, a wavelength is 254 nm, a column is HSS T3 (2.1 mm×100 mm, 1.8 μm), a column temperature is 35 degrees Celsius, a mobile phase solution is 0.1% formic acid aqueous solution, a flow rate is 0.3 mL/min, and a sample injection volume is 10 μL.

Figure 6:
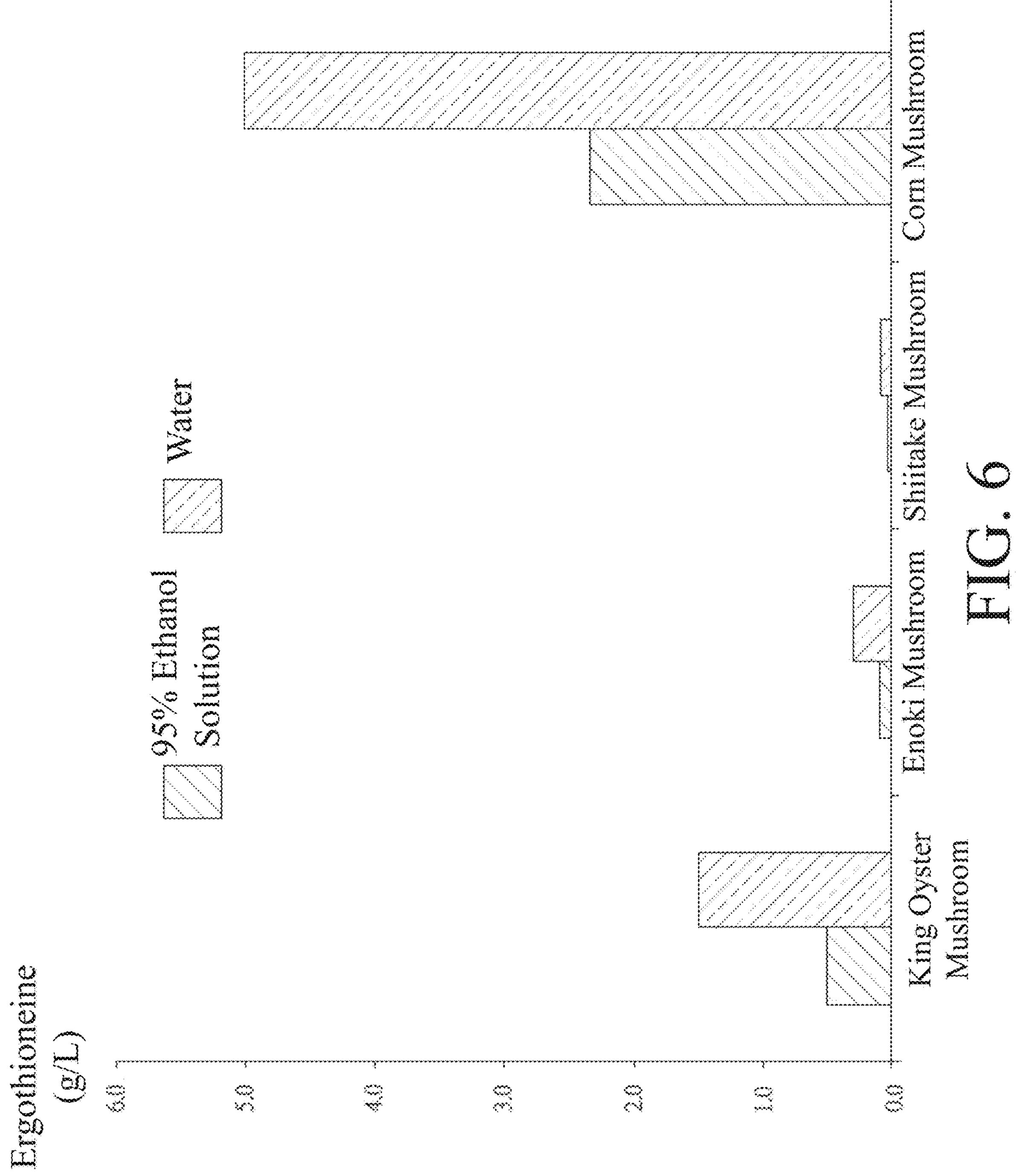
FIG. 6 is an experimental data graph of tested contents of ergothioneine of concentrated liquid made of mushrooms of various kinds.

The test result is described as follows. Refer to FIG. 6, and FIG. 6 is an experimental data graph of tested contents of ergothioneine of concentrated liquid made of mushrooms of various kinds. Specifically, FIG. 6 is the experimental data graph of contents of the ergothioneine extracted from various concentrated liquid made of the shiitake mushroom, enoki mushroom, king oyster mushroom and the corn mushroom when the solvent is the pure water and 95% ethanol solution. The analysis results show that compared with 95% ethanol solution, the content of ergothioneine obtained after extraction with pure water as the extraction solvent is relatively high. On the other hand, the concentrated liquid made of the corn mushroom has the highest ergothioneine content (about 2.3-5.0 g/L), the second is the concentrated liquid made of the king oyster mushroom (about 0.5-1.5 g/L), the third is the concentrated liquid made of the enoki mushroom (about 0.1-0.3 g/L), and the concentrated liquid made of the shiitake mushroom (about 0.01-0.07 g/L) has the lowest ergothioneine content.

In Embodiment 2, analysis of ergothioneine content in concentrated liquid made of fresh mushrooms of extraction solvents of different concentrations and different kinds is illustrated as follows.

The preparation of Embodiment 2 is illustrated as follows. At least one of the fresh king oyster mushroom (moisture content of 72%±3%) and fresh corn mushroom (moisture content 78%±3%) is taken as raw material, the raw material is weighted, and the fresh king oyster mushroom or the fresh corn mushroom of 1 kg is obtained. Then, the fresh king oyster mushroom or the fresh corn mushroom of 1 kg is added in extract solvent of 2.5 liters, and the extract solvent can be pure water, 50% ethanol solution, 70% ethanol solution or the 95% ethanol solution. Next, the above solution is uniformly mixed for 5 minutes through a homogenizer to obtain a homogeneous liquid. First extract is obtained by extracting the homogeneous liquid for 30 to 60 minutes through a food-grade ultrasonic extraction machine with an ultrasonic frequency range of 35 KHZ, a power of 180 W, and an extraction temperature of 60 degrees Celsius. The first extract is centrifuge at 4 degrees Celsius at a speed of 9000 rpm for 15 minutes, then the supernatant is collected, and the supernatant is the second extract made of the fresh king oyster mushroom or the fresh corn mushroom. Next, the second extract is concentrated to 1 liter under a decompression temperature of 40 to 60 degrees Celsius through a decompression concentrator, so as to obtain the concentrated liquid, wherein the concentrated liquid made of the king oyster mushroom is 0.2 times the weight of the original fresh king oyster mushroom, and the weight of the concentrated liquid made of the corn mushroom is concentrated to 0.15 times the weight of the original fresh corn mushroom.

Ergothioneine content test in Embodiment 2 is illustrated as follows.

An ultra-high pressure liquid chromatography (UPLC) is used to perform the content analysis of the ergothioneine on the concentrated liquid, and the ergothioneine obtained from each concentrated liquid is quantitatively analyzed through the calibration line prepared by ergothioneine standard substances with different concentrations. The analysis conditions of the ultra-high pressure liquid chromatography are as described as follows. The system is waters acquisition UPLC H-Class, the detector is a photodiode array detector, a wavelength is 254 nm, a column is HSS T3 (2.1 mm×100 mm, 1.8 μm), a column temperature is 35 degrees Celsius, a mobile phase solution is 0.1% formic acid aqueous solution, a flow rate is 0.3 mL/min, and a sample injection volume is 10 μL.

The test result is described as follows. See TABLE 3, and TABLE 3 shows the experimental data of the contents of the ergothioneine extracted from various concentrated liquid made of the fresh king oyster mushroom and the fresh corn mushroom when the solvent is the pure water, 50% ethanol solution, 70% ethanol solution and 95% ethanol solution. The analysis results show that the ergothioneine contents obtained by using 50% ethanol solution and 70% ethanol solution respectively are higher than the ergothioneine contents obtained by 95% ethanol solution and pure water respectively.

TABLE 3

| | Extraction solvent | | | |
|---|---|---|---|---|
| Ergothioneine (g/L) | 95% ethanol | 70% ethanol | 50% ethanol | Water |
| Fresh king oyster mushroom | 2.51 ± 0.26 | 3.80 ± 1.11 | 3.53 ± 0.51 | 2.92 ± 0.08 |
| Fresh corn mushroom | 4.22 ± 0.76 | 5.38 ± 0.86 | 5.21 ± 0.41 | 4.15 ± 0.16 |

In Embodiment 3, mushrooms of different kind are used to prepare concentrated liquid, and content of soluble solids, crude polysaccharides and total polyphenols in the concentrated liquid are tested.

The preparation of Embodiment 3 is illustrated as follows. At least one of the fresh king oyster mushroom (moisture content of 72%±3%) and fresh corn mushroom (moisture content 78%±3%) is taken as raw material, the raw material is weighted, and the fresh king oyster mushroom or the fresh corn mushroom of 1 kg is obtained. Then, the fresh king oyster mushroom or the fresh corn mushroom of 1 kg is added in extract solvent of 2.5 liters, and the extract solvent can be 50% ethanol solution or 70% ethanol solution. Next, the above solution is uniformly mixed for 5 minutes through a homogenizer to obtain a homogeneous liquid. First extract is obtained by extracting the homogeneous liquid for 30 to 60 minutes through a food-grade ultrasonic extraction machine with an ultrasonic frequency range of 35 KHZ, a power of 180 W, and an extraction temperature of 60 degrees Celsius. The first extract is centrifuge at 4 degrees Celsius at a speed of 9000 rpm for 15 minutes, then the supernatant is collected, and the supernatant is the second extract made of the fresh king oyster mushroom or the fresh corn mushroom. Next, the second extract is concentrated to 1 liter under a decompression temperature of 40 to 60 degrees Celsius through a decompression concentrator, so as to obtain the concentrated liquid, wherein the concentrated liquid made of the king oyster mushroom is 0.2 times the weight of the original fresh king oyster mushroom, and the weight of the concentrated liquid made of the corn mushroom is concentrated to 0.15 times the weight of the original fresh corn mushroom.

The content test of soluble solids, crude polysaccharides and total polyphenols in Embodiment 3 is illustrated as follows.

The concentrated liquid made of the fresh king oyster mushroom or the corn mushroom of 10 mL is dried at a temperature of 50 degrees Celsius to have a constant weight, and the dried residual is the content of the soluble solids. The content of the crude polysaccharides of the concentrated liquid made of the fresh king oyster mushroom or the fresh corn mushroom can be analyzed by using a phenol sulfuric acid method.

The test result is described as follows. See TABLE 4, in the concentrated liquid made of the fresh king oyster mushroom, the content of the soluble solids is about 34.9±2.14 g/L, the content of the crude polysaccharides is about 26.9±3.26 g/L, and the content of the total polyphenols is about 2.5±0.14 g/L; in the concentrated liquid made of the fresh corn mushroom, the content of the soluble solids is about 22.7±1.77 g/L, the content of the crude polysaccharides is about 18.2±1.76 g/L g/L, and the content of the total polyphenols is about 3.7±0.21 g/L.

TABLE 4

| | Soluble solids (g/L) | Crude polysaccharides (g/L) | Total polyphenols (g/L) |
|---|---|---|---|
| Fresh king oyster mushroom | 34.9 ± 2.14 | 26.9 ± 3.26 | 2.5 ± 0.14 |
| Fresh corn mushroom | 22.7 ± 1.77 | 18.2 ± 1.76 | 3.7 ± 0.21 |

In Embodiment 4, fresh mushroom fruiting bodies of different kinds are used to prepare a core layer with multiple holes and a yielding rate, a content of ergothioneine and a content of crude polysaccharides are tested.

The preparation of Embodiment 4 is illustrated as follows. At least one of the fresh king oyster mushroom (moisture content of 72%±3%) and fresh corn mushroom (moisture content 78%±3%) is taken as raw material, the raw material is weighted, and the fresh king oyster mushroom or the fresh corn mushroom of 1 kg is obtained. Then, place the fresh king oyster mushroom or the fresh corn mushroom in the freezer at −20 degrees Celsius to −80 degrees Celsius, and freeze for 16 hours. Next, freeze-dry the frozen fresh king oyster mushroom or fresh corn mushroom through a freeze dryer. Then, after grinding with a dry grinder, screen out grinded mushroom through a mesh screen having 80 meshes per inch, and collect the mushroom fruiting body particles (powder particle size less than 180 μm) as a core layer with multiple holes.

The test of the yielding rate, the content of ergothioneine and the content of crude polysaccharides are illustrated as follows. The yield rate test is to weigh the collected powder and calculate its percentage by weight of 1 kg of fresh king oyster mushroom or fresh corn mushroom. The content of the crude polysaccharides of the concentrated liquid made of the fresh king oyster mushroom or the fresh corn mushroom can be analyzed by using a phenol sulfuric acid method. An ultra-high pressure liquid chromatography (UPLC) is used to perform the content analysis of the ergothioneine on the concentrated liquid, and the ergothioneine obtained from each concentrated liquid is quantitatively analyzed through the calibration line prepared by ergothioneine standard substances with different concentrations. The analysis conditions of the ultra-high pressure liquid chromatography are as described as follows. The system is waters acquisition UPLC H-Class, the detector is a photodiode array detector, a wavelength is 254 nm, a column is HSS T3 (2.1 mm×100 mm, 1.8 μm), a column temperature is 35 degrees Celsius, a mobile phase solution is 0.1% formic acid aqueous solution, a flow rate is 0.3 mL/min, and a sample injection volume is 10 μL.

The test result is described as follows. Regarding the corn mushroom, the yielding rate of the mushroom fruiting body particles is 187.3±27.6 g/kg, the content of the ergothioneine is 0.57±0.04%, and the content of the crude polysaccharides is 37.75±1.43%. Regarding the king oyster mushroom, the yielding rate of the mushroom fruiting body particles is 262.2±41.1 g/kg, the content of the ergothioneine is 0.39±0.31%, and the content of the crude polysaccharides is 39.85±1.3%.

In Embodiment 5, the manufacturing of the microcapsule structure is illustrated.

The manufacturing of Embodiment 5 is illustrated as follows. The mushroom fruiting body particles (powder particle size less than 180 μm) of the king oyster mushroom and/or the corn mushroom are used to form the core layers with multiple holes. Then, spray the core layer powder in the air through the granulation step, and then use the spray manner to coat the concentrated liquid made of the king oyster mushroom and/or corn mushroom on the core layers. Next, use a mesh screen with 60 meshes per inch to screen out the core layers coated with multiple coating layers (powder particle size less than 250 μm) to obtain the microcapsule structure.

An ultra-high pressure liquid chromatography (UPLC) is used to perform the content analysis of the ergothioneine on the microcapsule structure, and the ergothioneine obtained from each microcapsule structure is quantitatively analyzed through the calibration line prepared by ergothioneine standard substances with different concentrations. The analysis conditions of the ultra-high pressure liquid chromatography are as described as follows. The system is waters acquisition UPLC H-Class, the detector is a photodiode array detector, a wavelength is 254 nm, a column is HSS T3 (2.1 mm×100 mm, 1.8 μm), a column temperature is 35 degrees Celsius, a mobile phase solution is 0.1% formic acid aqueous solution, a flow rate is 0.3 mL/min, and a sample injection volume is 10 μL.

The test result is described as follows. In TABLE 5, one part is 100 g. Regarding Group 1, when microcapsule structure is manufactured from the mushroom fruiting body particles of 1 part corn mushroom and the concentrated liquid made of 1 part king oyster mushroom, its ergothioneine content is 0.69±0.03%. Regarding Group 2, when microcapsule structure is manufactured from the mushroom fruiting body particles of 1 part king oyster mushroom and the concentrated liquid made of 1 part corn mushroom, its ergothioneine content is 0.45±0.02%. Regarding Group 3, when microcapsule structure is manufactured from the mushroom fruiting body particles of 2 part corn mushroom and 1 part king oyster mushroom and the concentrated liquid made of 0.7 part corn mushroom and 0.7 part king oyster mushroom, its ergothioneine content is 0.50±0.04%.

TABLE 5

| | Core layer | | Coating layer | | |
|---|---|---|---|---|---|
| | corn mushroom fruiting body particles | king oyster mushroom fruiting body particles | corn mushroom concentrated liquid | king oyster mushroom concentrated liquid | Microcapsule structure Ergothioneine % |
| Group 1 | 1 part | — | — | 1 part | 0.69 ± 0.03 |
| Group 2 | — | 1 part | 1 part | — | 0.45 ± 0.02 |
| Group 3 | 2 part | 1 part | 0.7 part | 0.7 part | 0.50 ± 0.04 |

In summary, the present disclosure has one of the following advantages compared with prior art and product.

An objective of the present disclosure is to provide a microcapsule structure comprising the core layer and the coating layer, wherein the core layer is formed by the mushroom fruiting body particles, and the surface of the coating layer is formed with polysaccharide, polyphenols and ergothioneine. Therefore, by increasing the surface area or filling capacity of the coating layer to increase the content of polysaccharide, polyphenols and ergothioneine contained in each microcapsule structure, it ensures that the microcapsule structure has the concentration of medicinal active ingredients that have health effects on the human body, and the inconvenience of having to eat a large amount of mushrooms in the past or the disadvantage of eating too much can be solved.

An objective of the present disclosure is to provide a usage of the ergothioneine microcapsule structure with the prebiotics for improving constipation and cleansing the colon. The microcapsule structure comprising the core layer and the coating layer, wherein the core layer is formed by the mushroom fruiting body particles, and the surface of the coating layer is formed with polysaccharide, polyphenols and ergothioneine. Therefore, manufacturers can adjust the concentration of medicinal active ingredients in the microcapsules themselves according to specific ethnic groups, times of taking or taking intervals, so as to meet the needs of different physiological conditions of different ages.

An objective of the present disclosure is to provide a manufacturing method of an ergothioneine microcapsule structure with prebiotics. By purposely selecting a specific preparation process sequence, the ratio of the weight of the coating layer to the weight of the core layer is controlled at 1:0.5 to 1:2.2, except for retaining relatively high contents of polysaccharide, polyphenols and ergothioneine, and also maintaining the release time and blood concentration of these medicinal active ingredients in the human body, so as to achieve the maximum effect.

While the present disclosure has been described by way of example and in terms of preferred embodiment, it is to be understood that the present disclosure is not limited thereto. To the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. A manufacturing method of an ergothioneine microcapsule structure with prebiotics, comprising steps as follows:

(a) providing mushroom fruiting body particles of at least a first mushroom fruiting body to form a core layer, wherein the core layer has multiple holes; and (b) using a granulation step to spray concentrated liquid on all or a part of surfaces of the core layer and the holes to form a coating layer, wherein the concentrated liquid comprises polysaccharide, polyphenols and ergothioneine, and a weight ratio of a weight of the coating layer over a weight of the core layer is 1:0.5 to 1:2.2.

2. The manufacturing method of the ergothioneine microcapsule structure with the prebiotics of claim 1, wherein a pulverization step, an extraction step and a concentration step are sequentially performed on a second mushroom fruiting body to form the concentrated liquid.

3. The manufacturing method of the ergothioneine microcapsule structure with the prebiotics of claim 2, wherein the pulverization step is to add the second mushroom fruiting body into a solvent to form a mushroom mixture and then to pulverize the second mushroom fruiting body of the mushroom mixture, wherein the mushroom mixture is 100 parts by weight, including 10-80 parts by weight of the second fruiting mushroom body, and the balance is the solvent, which is pure water or 20%-95% ethanol solution.

4. The manufacturing method of the ergothioneine microcapsule structure with the prebiotics of claim 2, wherein the extraction step comprises a hot water extraction step or an ultrasonic extraction step and a centrifugation step, wherein the hot water extraction step or the ultrasonic extraction step is to extract the pulverized mushroom mixture to obtain first extract, and the centrifugation step is to centrifuge the first extract to collect supernatant as second extract, wherein an extraction time of the extraction step is 0.5-24 hours.

5. The manufacturing method of the ergothioneine microcapsule structure with the prebiotics of claim 4, wherein the concentration step comprises a decompression concentration step or heating concentration step, which is used to concentrate the second extract to obtain the concentrated liquid, wherein a ratio of a weight of the concentrated liquid over a weight of the second mushroom fruiting body is 0.1 to 0.3.

6. The manufacturing method of the ergothioneine microcapsule structure with the prebiotics of claim 1, wherein a freeze-drying step and a dry-milling step are sequentially performed on the first mushroom fruiting body to obtain the mushroom fruiting body particles of the first mushroom fruiting body.

7. The manufacturing method of the ergothioneine microcapsule structure with the prebiotics of claim 6, wherein the freeze-drying step is to freeze the first mushroom fruiting body at a freezing temperature, and the freezing temperature is −20 degrees Celsius to −80 degrees Celsius.

8. The manufacturing method of the ergothioneine microcapsule structure with the prebiotics of claim 6, wherein the dry-milling step is to utilize a dry grinding manner to grind the frozen first mushroom fruiting body into the mushroom fruiting body particles of the first mushroom fruiting body.

9. The manufacturing method of the ergothioneine microcapsule structure with the prebiotics of claim 8, wherein the grinded first mushroom fruiting body is screened by using a first mesh screen to obtain the mushroom fruiting body particles of the first mushroom fruiting body, and the first mesh screen has 80 meshes per inch.

10. The manufacturing method of the ergothioneine microcapsule structure with the prebiotics of claim 8, wherein multiple core layers coated with multiple coating layers are screened by a second mesh screen to obtain the ergothioneine microcapsule structure with the prebiotics, and the second mesh screen has 60 meshes per inch.

11. The manufacturing method of the ergothioneine microcapsule structure with the prebiotics of claim 2, wherein each of the first mushroom fruiting body and the second mushroom fruiting body comprises at least one of a shiitake mushroom, an enoki mushroom, a king oyster mushroom and a corn mushroom.

* * * * *